United States Patent [19]

Akhtar

[11] Patent Number: 5,411,530
[45] Date of Patent: May 2, 1995

[54] SENSING ALGORITHM FOR ANTI-TACHYCARDIA DEVICES USING DUAL CHAMBER SENSING

[76] Inventor: Masood Akhtar, 1765 Brojan Dr., Elm Grove, Wis. 53122

[21] Appl. No.: 976,015
[22] Filed: Nov. 13, 1992
[51] Int. Cl.$^6$ .............................................. A61N 1/362
[52] U.S. Cl. .......................................... 607/14; 607/25
[58] Field of Search ...................... 607/4, 9, 14, 17, 18, 607/25

[56] References Cited

U.S. PATENT DOCUMENTS

| | | | |
|---|---|---|---|
| 4,144,892 | 3/1979 | Auerbach | 607/27 |
| 4,860,749 | 8/1989 | Lehmann | 607/14 X |
| 4,890,617 | 1/1990 | Markowitz et al. | 607/14 X |
| 5,086,772 | 2/1992 | Larnard et al. | 607/4 |
| 5,123,412 | 6/1992 | Betzold | 607/9 X |
| 5,179,949 | 1/1993 | Chirife | 607/9 |

Primary Examiner—Lee S. Cohen
Assistant Examiner—Jeffrey R. Jastrzab
Attorney, Agent, or Firm—Keck, Mahin & Cate

[57] ABSTRACT

An algorithm for classifying cardiac arrhythmias comprising multiple stages and dual chamber sensing. A first stage includes the steps of comparing ventricular and atrial rates and declaring that the heart is in atrial tachycardia or atrial fibrillation on the one hand, or that the heart is in ventricular fibrillation on the other hand. The second stage is entered if no determination is made in the first stage and, in particular, when the atrial rate equals the ventricular rate. A third stage is entered in which the heart is paced (ventricular, atrial or both) at a predetermined rate for a set period of time. Cardiac rhythm classification is made based on heart responses during and after pacing.

17 Claims, 4 Drawing Sheets

SENSING ALGORITHM FOR ANTI-TACHYCARDIA DEVICES USING DUAL CHAMBER SENSING

BACKGROUND OF THE INVENTION

The present invention relates to a cardiac sensing algorithm for identifying arrhythmias based on pacing diagnosis.

Poor discrimination between supraventricular tachycardia and ventricular tachycardia results in unnecessary delivery of shocks in patients with implantable defibrillators. This problem is seen in more than ten percent of patients with implantable cardiac defibrillators. Prior approaches to solve this problem have not focused on distinguishing between supraventricular tachycardia (SVT) and ventricular tachycardia (VT) using dual chamber sensing. One prior approach using dual chamber sensing only concentrates on distinguishing between sinus tachycardia (ST) and ventricular tachycardia. It is desirable that an implantable device be able to recognize and distinguish all forms of supraventricular tachycardia, as well as to discriminate sinus tachycardia from ventricular tachycardia.

SUMMARY OF THE INVENTION

It is a primary object of the present invention to provide a method for determining the type of cardiac arrhythmia based on responses to pacing pulses.

The algorithm according to the present invention is designed for use in an implantable antitachycardia cardioverter/defibrillator that requires accurate detection of underlying rhythm for proper functioning. In particular, the present invention provides for recognition of the nature of rhythm (normal vs. abnormal) and the precise type (VT vs. SVT) for accurate application of therapy. The algorithm employs dual chamber sensing and a pacing algorithm to improve sensing potential in a multistage technique towards tachycardia recognition, resulting in improved chances of accurate detection.

In particular, the algorithm according to the present invention is divided into three stages. In the first stage, the atrial and ventricular activity is sensed and the respective rates compared. If the atrial rate exceeds the ventricular rate, it is declared that the heart is in atrial tachycardia or atrial fibrillation. If the ventricular rate exceeds the atrial rate, it is declared that the heart is in ventricular tachycardia.

The second stage is entered when no determination is reached in stage one, specifically, when the atrial rate equals the ventricular rate. In this stage, the time interval between atrial depolarization and ventricular depolarization is examined and several determinations are made to arrive at an accurate diagnosis.

Finally, if no determination is made in stage two, the present invention features a third stage which is entered in which the heart is paced for a predetermined period of time and the responses to the pacing are examined to diagnose the heart rhythm.

The above and other objects and advantages will become more readily apparent when reference is made to the following description taken in conjunction with the accompanying drawings.

DETAILED DESCRIPTION OF THE DRAWINGS

Figure 1:
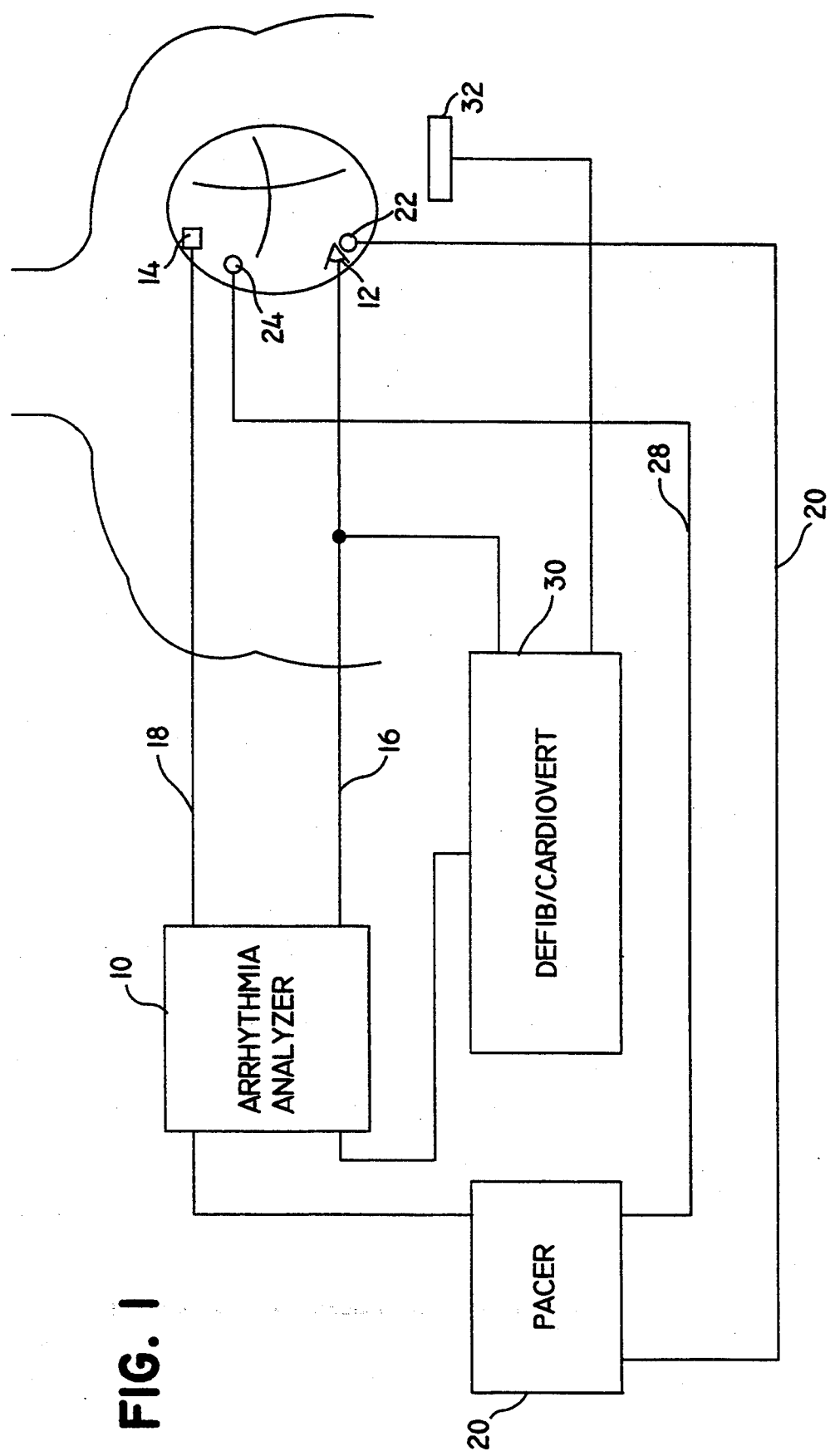
FIG. 1 is a block diagram of the system for performing the dual chamber sensing algorithm according to the present invention.

FIG. 1 illustrates, in general terms, the hardware for performing the dual chamber sensing algorithm according to the present invention. The detailed steps and computations of the sensing algorithm (shown in FIGS. 2 and 3A-3C) are performed by the arrhythmia analyzer shown at 10. A microprocessor or computer may be used as the arrhythmia analyzer 10. Ventricular and atrial sensing electrodes 12 and 14 are provided about the heart in the appropriate positions to sense the ventricular and atrial electrical activity respectively. These signals are fed to the arrhythmia analyzer 10 by the leads 16 and 18, respectively.

A pacer unit 20 is provided and connected to the arrhythmia analyzer 10 and to ventricular and atrial pacing electrodes 22 and 24 via leads 26 and 28, respectively. In addition, a defibrillation/cardioversion unit 30 is provided and connected to the arrhythmia analyzer 10. The defibrillation/cardioversion unit 30 is connected to ventricular electrode 12 which can serve as a sensing and defibrillation electrode and to the subcutaneous electrode 32. Additional defibrillation electrodes may be provided; however, the particular defibrillation electrode arrangement is not an essential requirement of the present invention.

Figure 2:
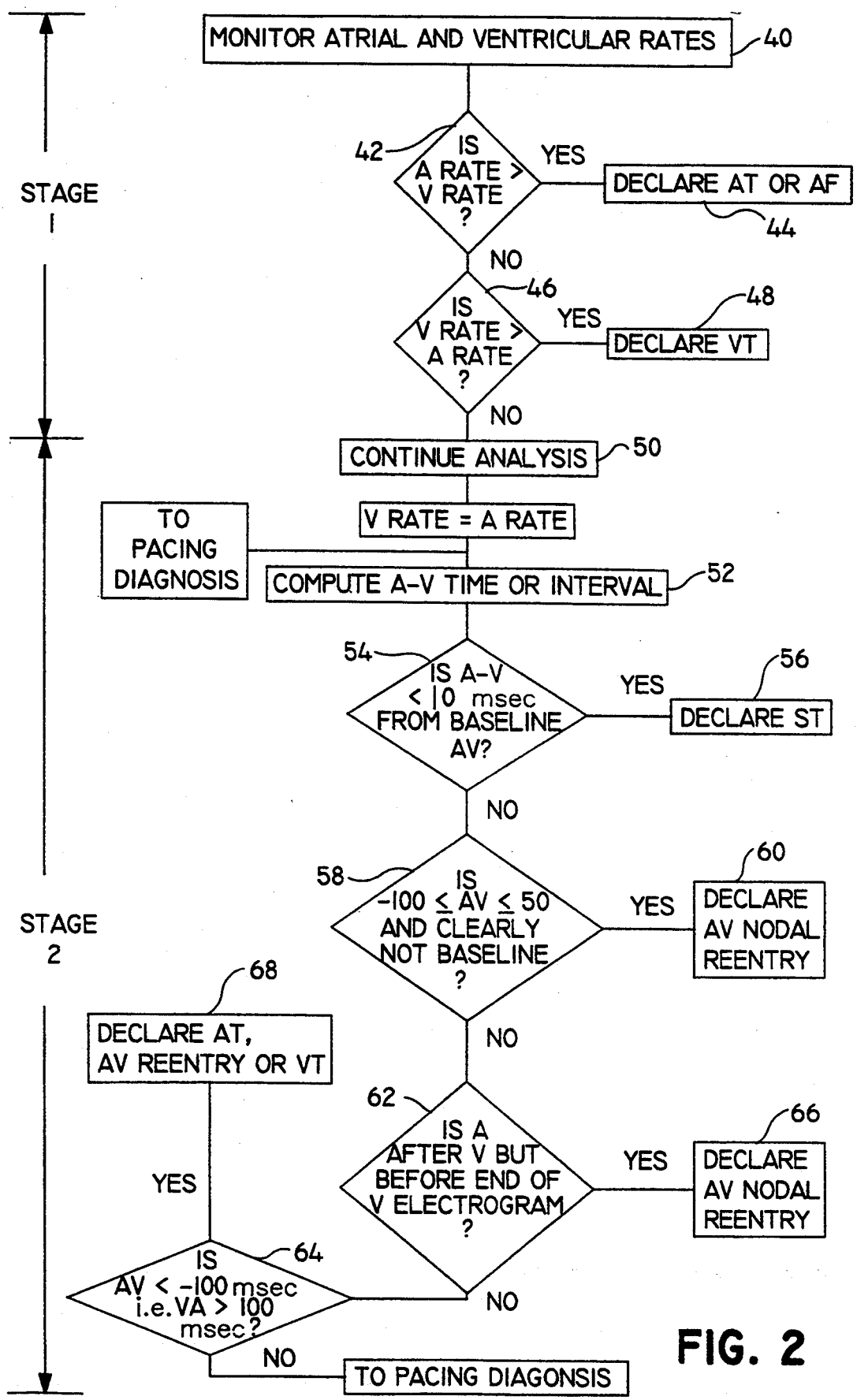
FIG. 2 is a flow diagram illustrating first and second stages of the dual chamber sensing algorithm according to the present invention.

The dual chamber sensing algorithm is implemented by software run on the machine embodying the arrhythmia analyzer 10. Referring now to FIG. 2, the first and second stages of the dual chamber sensing algorithm will be described. The first stage comprises steps 40-48 and the second stage comprises steps 50-68.

Initially, in step 40, the ventricular and atrial rates are derived from the signals detected by electrodes 12 and 14. In step 42, a comparison is made between the ventricular and atrial rates to determine if the atrial rate is greater than the ventricular rate. If so, it is declared in step 44 that the heart is in an atrial tachycardia or atrial fibrillation. Otherwise, the rates are compared again to determine if the ventricular rate is greater than the atrial rate in step 46. When the ventricular rate exceeds the atrial rate in step 46, it is declared that the heart is in a ventricular tachycardia in step 48. If the ventricular and atrial rates are equal, the algorithm continues at step 50 to either the pacing diagnosing routine (third stage of the algorithm) shown in FIGS. 3A-3C or to the second portion of the algorithm. The decision to go directly to the third stage or to the second stage may be based upon clinical and arrhythmia characteristics of a given patient. Preferably, the second stage is entered if no determination is made in stage one.

The first step in the second stage is to compute the A-V time interval in step 52. Next, in step 54 the computed A-V interval is compared with a baseline A-V value to determine if the computed value exceeds the baseline value by less than 10 msecs. If the criteria in step 54 is met, it is declared in step 56 that the heart is in a sinus tachycardia (ST). Otherwise, it is determined in step 58 whether the computed A-V interval falls between −100 msecs and 50 msecs and is clearly not equal to a baseline value. A positive value of less than 50 msecs on a negative value of the A-V time interval indicates that ventricular systole is occurring before atrial systole (actually a V-A interval). If the criteria in step 58 is met, it is declared in step 60 that the heart is in A-V nodal reentry.

Next, in step 62, it is determined whether atrial depolarization occurs after ventricular depolarization, but before the end of the ventricular electrogram (the signal sensed from the ventricle). If the test in step 62 proves positive, then it is declared in step 66 that the heart is in A-V nodal reentry. Otherwise, a test is made in step 64 to determine if the A-V interval is less than −100 msecs, meaning that ventricular systole preceded atrial systole by 100 msecs. If the A-V interval meets this test, then it is determined in step 68 that the heart is in atrial tachycardia, A-V reentry or ventricular tachycardia. If not, then the algorithm jumps to the third stage, called the pacing diagnosis routine.

Figure 3A:
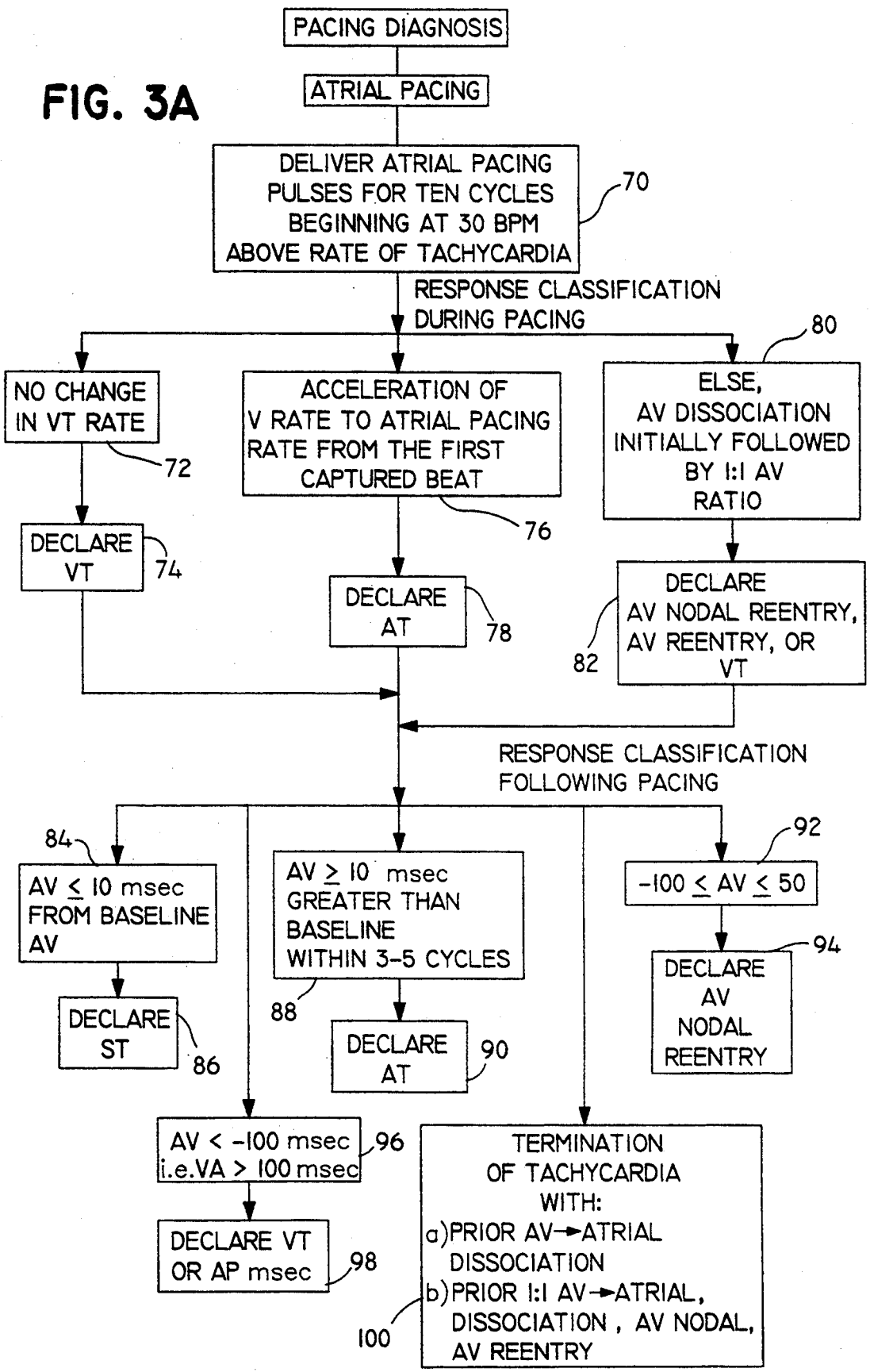
FIGS. 3A-3C are flow diagrams illustrating a third stage in which pacing diagnosis is performed as part of the dual chamber sensing algorithm according to the present invention.
Figure 3B:
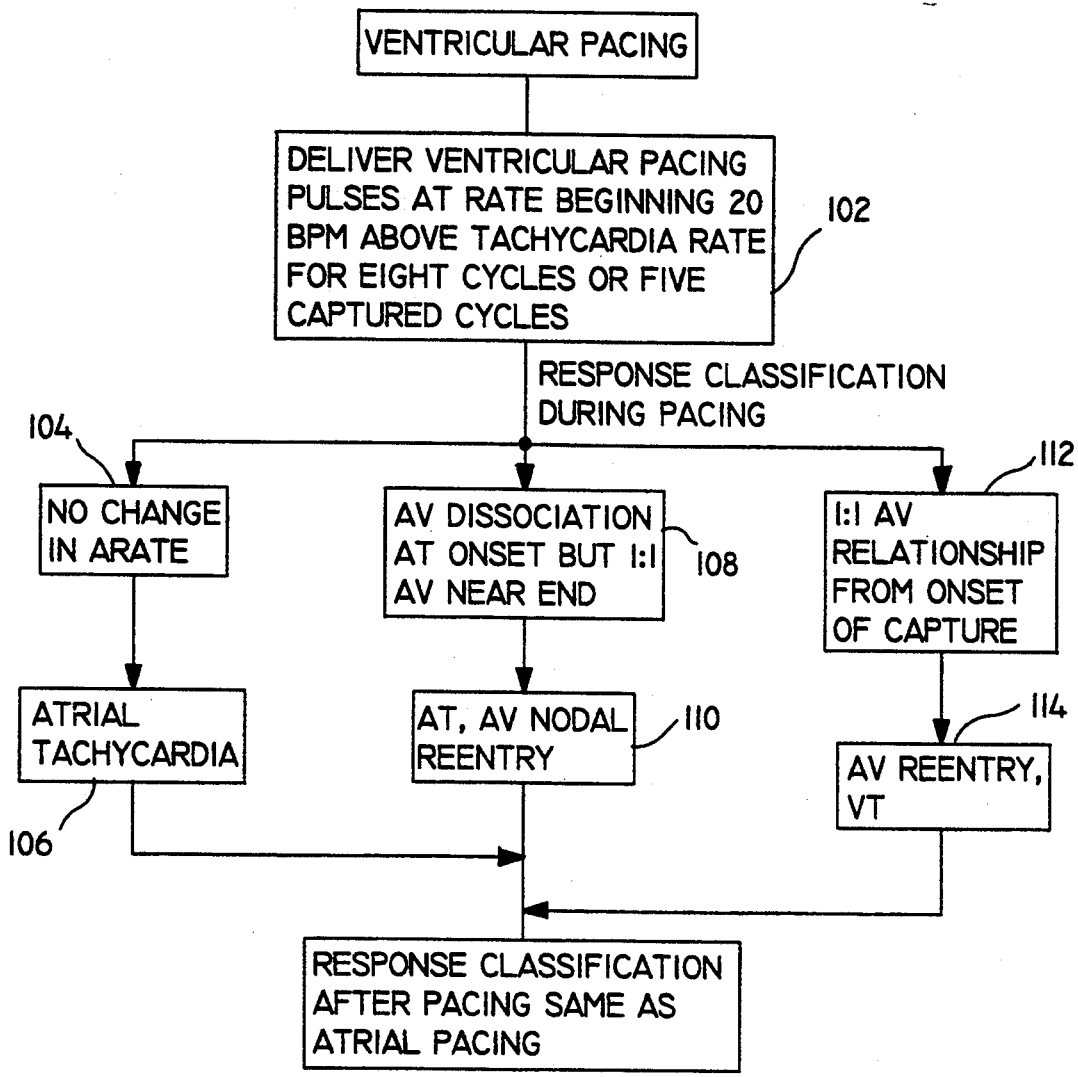
Figure 3C:
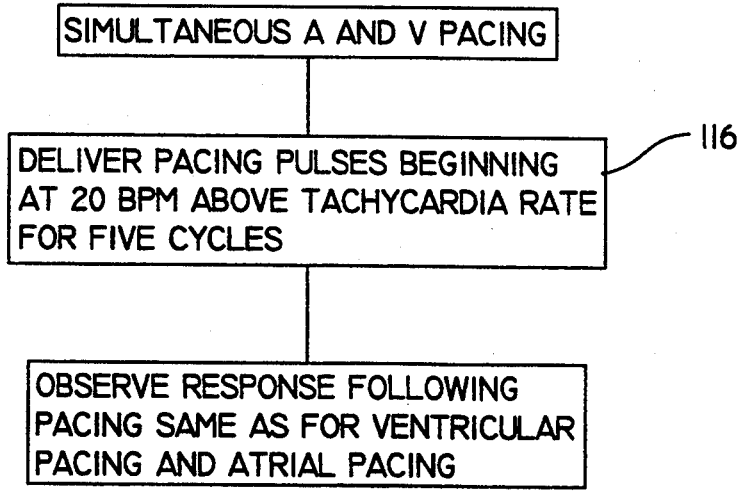

The third stage, called the pacing diagnosis routine, is illustrated in FIGS. 3A–3C. FIG. 3A illustrates the details of the atrial pacing diagnosis routine. Initially, in step 70 atrial pacing pulses are delivered to the heart at a rate approximately 20–40 (programmable) beats-per-minutes (BPM) above the sensed tachycardia rate for ten cardiac cycles. During the ten cycles of pacing, the responses of the heart are monitored and classified.

Specifically, the ventricular rate is monitored in step 72 and if there is no change as a result of the atrial pacing pulses, then it is declared in step 74 that the heart is in ventricular tachycardia. Next, it is determined in step 76 whether the ventricular rate accelerated as a result of the atrial pacing pulses from the first captured beat. If so, it is declared in step 78 that the heart is in atrial tachycardia. Finally, if no match is made in steps 72 and 76, then it is determined in step 80 whether there is A-V dissociation initially followed by a 1:1 A-V ratio. If so, then it is declared in step 82 that the heart is in A-V nodal reentry, A-V reentry, or ventricular tachycardia.

In addition, the responses to the atrial pacing are monitored after the ten cycles of pacing. In step 84, if the A-V interval is less than or equal to 10 msecs, then it is declared in step 86 that the heart is in sinus tachycardia. In step 88, if the A-V interval is more than 10 msecs greater than the baseline A-V interval within 3–5 cardiac cycles, then it is declared in step 90 that the heart is in an atrial tachycardia. In step 92, if the A-V interval is less than or equal to 50 msecs but greater than or equal to −100 msecs, then it is declared in step 94 that the heart is in A-V nodal reentry. Furthermore, if the A-V interval is greater than 100 msecs as determined in step 96, then it is declared in step 98 that the heart is in ventricular tachycardia. Finally, in step 100, if the atrial pacing pulses terminated the tachycardia with prior A-V block during pacing, then it is declared that the heart is in atrial tachycardia. Otherwise, if the atrial pacing pulses terminated the tachycardia with prior 1:1 A-V conduction, then it is determined that the heart is in atrial tachycardia or A-V nodal reentry.

FIG. 3B illustrates the routine for ventricular pacing diagnosis. In step 102, ventricular pacing pulses are initially delivered to the heart at a rate approximately 20 BPM greater than the sensed tachycardia rate for eight cycles or five captured cycles. Like the atrial pacing diagnosis, the responses to the ventricular pacing are monitored during the application of the pacing pulses. If there is no change detected in the atrial rate in step 104, then it is declared that the heart is in atrial tachycardia in step 106. If it is determined in step 108 that the heart is in atrial dissociation at the onset of the pulses but in a 1:1 ratio near the end of the pulses, then it is determined in step 110 that the heart is in atrial tachycardia, or A-V nodal reentry. Finally, if the heart has a 1:1 A-V relationship from the onset of capture in step 112, then it is determined that the heart is in A-V reentry or ventricular tachycardia 114.

In addition, the responses after application of the pacing pulses are examined and classified in the same manner as that in the atrial pacing diagnosis routine, illustrated by steps 84–100 in FIG. 3A.

FIG. 3C illustrates the simultaneous atrial/ventricular pacing diagnosis routine. In step 116, pacing pulses are simultaneously delivered to an atrium and ventricle of the heart at a rate approximately 20 BPM above the tachycardia rate for five to eight cycles. The responses to the pacing pulses are examined in the same manner as shown in stages 52–68 (FIG. 2).

The foregoing description is intended by way of example only and is not intended to limit the present invention in any way except as set forth in the following claims.

I claim:

1. A method for sensing cardiac activity and classifying a condition of a heart comprising the steps of:
   of first stage of sensing atrial and ventricular depolarization rates of the heart;
   comparing the atrial depolarization rate with the ventricular depolarization rate;
   a second stage implemented if the atrial depolarization rate equals the ventricular depolarization rate, said second stage including the steps of:
   computing an A-V time interval;
   comparing the A-V time interval with a baseline value;
   declaring the heart condition based on the difference between the A-V time interval and the baseline value; and
   a third stage implemented if no declaration is made in said second stage, said third stage including the steps of:
   pacing the heart at a predetermined rate for a predetermined period of time;
   monitoring a response to said step of pacing during and after said predetermined period of time; and
   declaring a specific arrhythmia based on the response of the heart during said step of pacing and after said predetermined period of time.

2. The method of claim 1, wherein said second stage further comprises the steps of:
   declaring that the heart is in sinus tachycardia if said A-V time interval differs from said baseline value by a predetermined amount;
   determining if said A-V time interval is within a predetermined threshold interval if said A-V time interval differs from said baseline value by more than said predetermined amount;
   declaring that the heart is in A-V nodal reentry if said A-V time interval is within said predetermined threshold interval;

determining if atrial depolarization occurs before ventricular depolarization but before an end of a ventricular electrogram if said A-V time interval is outside of said predetermined threshold interval;

declaring that the heart is in A-V nodal reentry if atrial depolarization occurs before ventricular depolarization but before the end of the ventricular electrogram;

3. The method of claim 2, wherein said second stage further comprises the steps of:

comparing the A-V time interval with a predetermined threshold value; and declaring that the heart is in atrial tachycardia, A-V nodal reentry or ventricular tachycardia if said A-V interval is less than said predetermined threshold value.

4. The method of claim 1, wherein said step of pacing of said third stage comprises the step of pacing an atrium of the heart at said predetermined rate for said predetermined period of time, and said step of monitoring comprises the steps of determining if the ventricular depolarization rate accelerates or does not change during said step of pacing, and said step of declaring of said third stage comprises the steps of declaring that the heart is in ventricular tachycardia if the ventricular depolarization rate does not change, declaring that the heart is in atrial tachycardia if the ventricular depolarization rate accelerates, or declaring that the heart is in A-V nodal reentry or ventricular tachycardia if the ventricular depolarization rate decelerates.

5. The method of claim 4, wherein said step of monitoring after pacing of said third stage comprises the step of comparing an A-V time interval after pacing with said predetermined rate, and said step of declaring comprises the step of declaring that the heart is in sinus tachycardia if said A-V time interval after pacing differs from said baseline value by said predetermined amount or declaring that the heart is in atrial tachycardia if said A-V time interval after pacing differs from said baseline value more than said predetermined amount.

6. The method of claim 4, wherein said step of monitoring after pacing further comprises the steps of:

determining if said A-V time interval is within a predetermined threshold value if said A-V time interval differs from said baseline value by more than said predetermined amount;

comparing the A-V time interval with a predetermined threshold value if atrial depolarizations do not occur before ventricular depolarizations; and wherein said step of declaring further comprises the steps of:

declaring that the heart is in atrial tachycardia, A-V nodal reentry or ventricular tachycardia if said A-V interval is less than said predetermined threshold value; and declaring that the heart is in A-V nodal reentry if said A-V time interval is within said predetermined threshold value.

7. The method of claim 1, wherein said step of pacing of said third stage comprises the step of pacing a ventricle of the heart at said predetermined rate for said predetermined period of time, and said step of monitoring comprises the steps of determining if the ventricular depolarization rate accelerates or does not change during said step of pacing, and said step of declaring of said third stage comprises the steps of declaring that the heart is in ventricular tachycardia if the ventricular depolarization rate does not change, declaring that the heart is in atrial tachycardia if the ventricular depolarization rate accelerates, or declaring that the depolarization is in A-V nodal reentry or ventricular tachycardia if the ventricular heart rate decelerates.

8. The method of claim 7, wherein said step of monitoring after pacing comprises the step of comparing an A-V time interval after pacing with said baseline value, and said step of declaring comprises the step of declaring that the heart is in sinus tachycardia if said A-V time interval after pacing differs from said baseline value by said predetermined amount or declaring that the heart is in atrial tachycardia if said A-V time interval after pacing differs from said baseline value more than said predetermined amount.

9. The method of claim 7, wherein said step of monitoring after pacing further comprises the steps of:

determining if said A-V time interval is within a predetermined threshold interval if said A-V time interval differs from said baseline value by more than said predetermined amount;

comparing the A-V time interval with a predetermined threshold value if atrial depolarizations do not occur before ventricular depolarizations; and wherein said step of declaring further comprises the steps of:

declaring that the heart is in atrial tachycardia, A-V nodal reentry or ventricular tachycardia if said A-V interval is less than said predetermined threshold value; and declaring that the heart is in A-V nodal reentry if said A-V time interval is within said predetermined threshold value.

10. The method of claim 1, wherein said predetermined rate of said step of pacing is a predetermined amount above a tachycardia rate of the heart.

11. A method of sensing cardiac activity and classifying heart rhythm comprising the steps of:

pacing a heart at a predetermined rate for a predetermined period of time;

monitoring a response to said step of pacing during and after said predetermined period of time and detecting an A-V time interval after pacing then comparing said A-V time interval with a baseline value; and declaring a heart condition based on the response of the heart during said step of pacing and after said predetermined period of time, and declaring that the heart is in sinus tachycardia if said A-V time interval after pacing differs from said baseline value by said predetermined amount or declaring that the heart is in atrial tachycardia if said A-V time interval after pacing differs from said baseline value by more than said predetermined amount.

12. A method of sensing cardiac activity and classifying heart rhythm comprising the steps of:

pacing a heart at a predetermined rate for a predetermined period of time; monitoring a response to said step of pacing during and after said predetermined period of time, said step of monitoring further comprising the steps of:

determining if an A-V time interval is within a predetermined threshold interval if said A-V time interval differs from a baseline value by more than said predetermined amount;

comparing the A-V time interval with a predetermined threshold value if atrial depolarizations do not occur before ventricular depolarizations; and wherein said step of declaring further comprises the steps of:

declaring that the heart is in atrial tachycardia, A-V nodal reentry or ventricular tachycardia if said A-V interval is less than said predetermined threshold value; and declaring that the heart is in A-V nodal reentry if said A-V time interval is within said predetermined threshold interval; and declaring a heart condition based on the response of the heart during said step of pacing and after said predetermined period of time.

13. A method of sensing cardiac activity and classifying heart rhythm comprising the steps of:

pacing a heart at a predetermined rate for a predetermined period of time by pacing a ventricle of the heart at said predetermined rate for said predetermined period of time;

monitoring a response to said step of pacing during and after said predetermined period of time, and determining if the ventricular depolarization rate accelerates or does not change during said step of pacing; and declaring a heart condition based on the response of the heart during said step of pacing and after said predetermined period of time, and declaring that the heart is in ventricular tachycardia if the ventricular depolarization rate does not change, declaring that the heart is in atrial tachycardia if the ventricular depolarization rate accelerates, or declaring that the heart is in A-V nodal reentry or ventricular tachycardia if the ventricular depolarization rate decelerates.

14. The method of claim 13, wherein said step of monitoring after pacing comprises the step of detecting an A-V time interval then comparing the A-V time interval with a baseline value, and said step of declaring comprises the step of declaring that the heart is in sinus tachycardia if said A-V time interval after pacing differs from said baseline value by said predetermined amount or declaring that the heart is in atrial tachycardia if said A-V time interval after pacing differs from said baseline value by more than said predetermined amount.

15. The method of claim 13, wherein said step of monitoring after pacing further comprises the steps of:

determining if an A-V time interval is within a predetermined threshold interval if said A-V time interval differs from a baseline value by more than said predetermined amount;

comparing the A-V time interval with a predetermined threshold value if atrial depolarizations do not occur before ventricular depolarizations; and wherein said step of declaring further comprises the steps of:

declaring that the heart is in atrial tachycardia, A-V nodal reentry or ventricular tachycardia if said A-V interval is less than said predetermined threshold value; and declaring that the heart is in A-V nodal reentry if said A-V time interval is within said predetermined threshold interval.

16. A method of sensing cardiac activity and classifying heart rhythm comprising the steps of:

pacing a heart at a predetermined amount above a tachycardia rate of the heart for a predetermined period of time;

monitoring a response to said step of pacing during and after said predetermined period of time; and declaring a heart condition based on the response of the heart during said step of pacing and after said predetermined period of time.

17. A method of sensing cardiac activity and classifying heart rhythm comprising the steps of:

pacing a heart at a predetermined rate for a predetermined period of time;

monitoring a response to said step of pacing during and after said predetermined period of time; and declaring a heart condition based on the response of the heart during said step of pacing and after said predetermined period of time.

* * * * *